(12) United States Patent
Zhao et al.

(10) Patent No.: US 6,872,724 B2
(45) Date of Patent: Mar. 29, 2005

(54) POLYMORPHS WITH TYROSINE KINASE ACTIVITY

(75) Inventors: Matthew M. Zhao, Edison, PA (US); Mark T. Bilodeau, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 63 days.

(21) Appl. No.: 10/607,091

(22) Filed: Jun. 26, 2003

(65) Prior Publication Data
US 2004/0023980 A1 Feb. 5, 2004

Related U.S. Application Data

(60) Provisional application No. 60/398,238, filed on Jul. 24, 2002.

(51) Int. Cl.$^7$ .................. C07D 401/14; A61K 31/496
(52) U.S. Cl. .................. 514/253.1; 514/21; 514/23; 544/364
(58) Field of Search .................. 514/21, 23, 253.1; 544/364

(56) References Cited

U.S. PATENT DOCUMENTS

| | | | |
|---|---|---|---|
| 4,649,146 A | 3/1987 | Takaya et al. | |
| 4,788,195 A | 11/1988 | Torley et al. | |
| 4,876,252 A | 10/1989 | Torley et al. | |
| 5,463,071 A | 10/1995 | Himmelsbach et al. | |
| 5,516,775 A | 5/1996 | Zimmermann et al. | |
| 5,521,184 A | 5/1996 | Zimmermann | |
| 5,530,000 A | 6/1996 | Sanfilippo et al. | |
| 5,863,924 A | 1/1999 | Berger et al. | |
| 5,952,331 A | 9/1999 | Berger et al. | |
| 5,958,934 A | 9/1999 | Berger et al. | |
| 6,586,423 B2 | 7/2003 | Bilodeau et al. | |
| 6,586,424 B2 | 7/2003 | Bilodeau et al. | |

FOREIGN PATENT DOCUMENTS

| | | |
|---|---|---|
| DE | 19548415 | 6/1997 |
| DE | 19824175 A1 | 5/1998 |
| EP | 0 384 250 | 8/1990 |
| EP | 0 564 409 A1 | 10/1993 |
| EP | 1040831 A2 | 10/2000 |
| JP | 6475475 A | 3/1989 |
| JP | 7149745 A | 6/1995 |
| WO | WO 94/01423 | 1/1994 |
| WO | WO 95/09847 | 4/1995 |
| WO | WO 95/09852 | 4/1995 |
| WO | WO 95/33750 | 12/1995 |
| WO | WO 95/35275 | 12/1995 |
| WO | WO 95/35276 | 12/1995 |
| WO | WO 97/19065 | 5/1997 |
| WO | WO 97/44326 | 11/1997 |
| WO | WO 98/32753 | 7/1998 |
| WO | WO 99/21845 | 5/1999 |
| WO | WO 99/64418 | 12/1999 |
| WO | WO 99/65884 | 12/1999 |
| WO | WO 00/09495 | 2/2000 |
| WO | WO 00/12497 | 3/2000 |
| WO | WO 00/39101 | 7/2000 |
| WO | WO 00/62778 | 10/2000 |
| WO | WO 01/17995 | 3/2001 |
| WO | WO 01/56567 | 8/2001 |
| WO | WO 01/70738 | 9/2001 |

OTHER PUBLICATIONS

J. Rak et al. Cancer Research, 55:4575–4580, 1995.
G. Gasparini and A.L. Harris, J. Clin. Oncol., 1995, 13:765–782.
M. Toi et al., Japan. J. Cancer Res., 1994, 85:1045–1049.
A.J. Dickinson et al., Br. J. Urol., 1994, 74:762–766.
L.M. Ellis et al., Surgery, 1996, 120(5):871–878.
J.K. Williams et al., Am. J. Surg., 1994, 168:373–380.
A. Amirkhosravi et al., Platelets, 10:285–292 (1999).
S.P. Gunningham, et al., Can. Research, 61: 3206–3211 (2001).
A. Giatromanolaki et al., J. Pathol. 2001; 194:101–108.
Michael Detmar, J. Dermatological Sci., 24 Suppl. 1, S78–S84 (2000).
Hasegawa et al., Skeletal Radiol., vol. 28, pp. 41–45, 1999.
Brockelsby et al., Laboratory Investigation 79:1101–1111 (Sep. 1999).
Paul et al., Nature Med 7:222–227 (2001).
Matsuyama et al., J. Neurol. Sci. 186:75–79 (2001).
van der Flier et al., J. Infectious Diseases, 183:149–153 (2001).
Stephen K. Smith, Trends in Endocrinology & Metabolism, vol. 12, No. 4, pp. 147–151, May/Jun. 2001.
Levis et al., Blood, vol. 98, No. 3, pp. 885–887 (2001).
Rajesh K. Jain, Nature Medicine, vol. 7, No. 9, pp. 987–989 (Sep. 2001).
Giulio Jori, Lasers Med. Sci., 1990; 5: 115–120.
Chuannong Zhou, J. Photochem. and Photobiol. 1989; 3: 299–318.
Hendrich et al., Knee Surg Sports Traumatol Arthroscopy 5: 58–63 (1997).
Hall et al., Am J Hum Genet 61:785–789, 1997.
Li et al., Gene Therapy, 1998; 5:1105–1113.
Fathallah–Shaykh et al., J Immunol 2000; 164:217–222.
Dougherty et al., J. Natl. Cancer Inst., 1998, 90(12): 889–905.

(Continued)

*Primary Examiner*—Thomas C. McKenzie
(74) *Attorney, Agent, or Firm*—David A. Muthard; Mark R. Daniel

(57) ABSTRACT

The present invention relates to active polymorphs of 4-[2-(5-cyano-thiazol-2-ylamino)-pyridin-4-ylmethyl]-piperazine-1-carboxylic acid methylamide which inhibit, regulate and/or modulate tyrosine kinase signal transduction, compositions which contain these compounds, and methods of using them to treat tyrosine kinase-dependent diseases and conditions, such as angio-genesis, cancer, tumor growth, atherosclerosis, age related macular degeneration, diabetic retinopathy, retinal ischemia, macular edema, inflammatory diseases, and the like in mammals.

7 Claims, 2 Drawing Sheets

OTHER PUBLICATIONS

Van Bruggen et al., J. Clin. Invest,. 104:1613–1620 (1999).
Gerber et al., Nature Medicine, vol. 5, No. 6, pp. 623–628, 1999.
David A. Greenberg, Drug News Perspect 1 1(5):265–270 (1998).
Nakagawa et al., FEBS Let. 473:161–164 (2000).
M. Shibuya et al., Oncogene, vol. 5, pp. 519–524 (1990).
Stem Cells, vol. 12, pp. 1–6 (1994), by T. R. Burke, Jr.
Molecular Cell, vol. 4, pp. 915–924 (1999), by B. Eliceiri, et al.
Oncogene, vol. 6, pp. 1677–1683 (1991), by B. Terman, et al.
Nature Biotech., vol. 17, pp. 963–968 (1999), by V. Brower.
Nature, vol. 407, pp. 242–248 (2000), by G. Yancopoulos, et al.
Nature, vol. 407, pp. 249–257 (2000), by P. Carmeliet, et al.
Endocrinology, Abstract, vol. 141, No. 5, pp. 1667–1674 (2000), by M. Deckers, et al.
Chem. Abst., vol. 109, No. 8, p. 634 (1988), N. A. Shvink.
Chem. Abstr., vol. 111, No. 15, p. 761 (1989), by M. Tsuji.
Chem. Abstr., vol. 111, No. 21, p. 765 (1989), by M. Santus.
Chem. Abstr., vol. 126, No. 21, p. 666 (1997), by C. S. Ra.
Chem. Abstr., vol. 101, No. 11, p. 33 (1984), by H. Nagatomi.
Abstract, Indian J. Chem., Sect. G (1986), 25B(4), 452–5, S.E. Kulkarni, et al.
Abstract, Eur. Pat. Appl., 35 pp., T. Takaya, et al.
Abstract, Acta Pol. Pharm. (1980), 37(3), 293–300, M. Santus.
Abstract, Phamacol. Res. Commun., (1982), 14(4), 359–68, M. Tandon, et al.
Abstract, Pharmazie (1975), 30(3), 141–7, G. Wagner, et al.
Annual Reports in Med. Chem., vol. 27, pp. 139–148 (1992), Mitchell, et al.
Abstract, Hematol Oncol. Clin. North Am., Oct., 2002; 16(5) 1173–87, Rosen.
Abstract, Pharmacol. Ther. 1998, Feb. 77(2): 81–114, Lawrence et al.
Ann. NY Acad. Sci. 979:80–93 (2002), Luttun et al.
Cancer Research, 60, 970–975, Feb. 15, 2000, Wedge et al.
Exp. Opin. Ther. Patents, vol. 7(6), 571–588, 1997, Traxler.
Cecil Textbook of Medicine, 20th Edition, vol. 1, 1004–10, 1996, Simone.

POLYMORPHS WITH TYROSINE KINASE ACTIVITY

This application claims the benefit of U.S. Provisional Application No. 60/398,238, filed Jul. 24, 2002.

BACKGROUND OF THE INVENTION

The present invention relates to active polymorphs of 4-[2-(5-cyano-thiazol-2-ylamino)-pyridin-4-ylmethyl]-piperazine-1-carboxylic acid methylamide, which inhibit, regulate and/or modulate tyrosine kinase signal transduction, compositions which contain these polymorphs, and methods of using them to treat tyrosine kinase-dependent diseases and conditions, such as angiogenesis, cancer, tumor growth, atherosclerosis, age related macular degeneration, diabetic retinopathy, retinal ischemia, macular edema, inflammatory diseases, and the like in mammals.

Tyrosine kinases are a class of enzymes that catalyze the transfer of the terminal phosphate of adenosine triphosphate to tyrosine residues in protein substrates. Tyrosine kinases play critical roles in signal transduction for a number of cell functions via substrate phosphorylation. Though the exact mechanisms of signal transduction is still unclear, tyrosine kinases have been shown to be important contributing factors in cell proliferation, carcinogenesis and cell differentiation.

Tyrosine kinases can be categorized as receptor type or non-receptor type. Receptor type tyrosine kinases have an extracellular, a transmembrane, and an intracellular portion, while non-receptor type tyrosine kinases are wholly intracellular.

The receptor-type tyrosine kinases are comprised of a large number of transmembrane receptors with diverse biological activity. In fact, about twenty different subfamilies of receptor-type tyrosine kinases have been identified. One tyrosine kinase subfamily, designated the HER subfamily, is comprised of EGFR, HER2, HER3, and HER4. Ligands of this subfamily of receptors include epithileal growth factor, TGF-α, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-α and β receptors, CSFIR, c-kit and FLK-II. Then there is the FLK family which is comprised. of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., *DN&P* 7(6):334–339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen *Oncogene*, 8:2025–2031 (1993), which is hereby incorporated by reference.

Both receptor-type and non-receptor type tyrosine kinases are implicated in cellular signaling pathways leading to numerous pathogenic conditions, including cancer, psoriasis and hyperimmune responses.

Several receptor-type tyrosine kinases, and the growth factors that bind thereto, have been suggested to play a role in angiogenesis, although some may promote angiogenesis indirectly (Mustonen and Alitalo, *J. Cell Biol.* 129:895–898, 1995). One such receptor-type tyrosine kinase is fetal liver kinase 1 or FLK-1. The human analog of FLK-1 is the kinase insert domain-containing receptor KDR, which is also known as vascular endothelial cell growth factor receptor 2 or VEGFR-2, since it binds VEGF with high affinity. Finally, the murine version of this receptor has also been called NYK (Oelrichs et al., *Oncogene* 8(1):11–15, 1993). VEGF and KDR are a ligand-receptor pair that play an important role in the proliferation of vascular endothelial cells, and the formation and sprouting of blood vessels, termed vasculogenesis and angiogenesis, respectively.

Angiogenesis is characterized by excessive activity of vascular endothelial growth factor (VEGF). VEGF is actually comprised of a family of ligands (Klagsburn and D'Amore, *Cytokine & Growth Factor Reviews* 7:259–270, 1996). VEGF binds the high affinity membrane-spanning tyrosine kinase receptor KDR and the related fms-like tyrosine kinase-1, also known as Flt-1 or vascular endothelial cell growth factor receptor 1 (VEGFR-1). Cell culture and gene knockout experiments indicate that each receptor contributes to different aspects of angiogenesis. KDR mediates the mitogenic function of VEGF whereas Flt-1 appears to modulate non-mitogenic functions such as those associated with cellular adhesion. Inhibiting KDR thus modulates the level of mitogenic VEGF activity. In fact, tumor growth has been shown to be susceptible to the antiangiogenic effects of VEGF receptor antagonists. (Kim et al., Nature 362, pp. 841–844, 1993).

Solid tumors can therefore be treated by tyrosine kinase inhibitors since these tumors depend on angiogenesis for the formation of the blood vessels necessary to support their growth. These solid tumors include histiocytic lymphoma, cancers of the brain, genitourinary tract, lymphatic system, stomach, larynx and lung, including lung adenocarcinoma and small cell lung cancer. Additional examples include cancers in which overexpression or activation of Raf-activating oncogenes (e.g., K-ras, erb-B) is observed. Such cancers include pancreatic and breast carcinoma. Accordingly, inhibitors of these tyrosine kinases are useful for the prevention and treatment of proliferative diseases dependent on these enzymes.

The angiogenic activity of VEGF is not limited to tumors. VEGF accounts for most of the angiogenic activity produced in or near the retina in diabetic retinopathy. This vascular growth in the retina leads to visual degeneration culminating in blindness. Ocular VEGF mRNA and protein are elevated by conditions such as retinal vein occlusion in primates and decreased $pO_2$ levels in mice that lead to neovascularization. Intraocular injections of anti-VEGF monoclonal antibodies or VEGF receptor immunofusions inhibit ocular neovascularization in both primate and rodent models. Regardless of the cause of induction of VEGF in human diabetic retinopathy, inhibition of ocular VEGF is useful in treating the disease.

Expression of VEGF is also significantly increased in hypoxic regions of animal and human tumors adjacent to areas of necrosis. VEGF is also upregulated. by the expression of the oncogenes ras, raf, src and mutant p53 (all of which are relevant to targeting cancer). Monoclonal anti-VEGF antibodies inhibit the growth of human tumors in nude mice. Although these same tumor cells continue to express VEGF in culture, the antibodies do not diminish their mitotic rate. Thus tumor-derived VEGF does not function as an autocrine mitogenic factor. Therefore, VEGF contributes to tumor growth in vivo by promoting angiogenesis through its paracrine vascular endothelial cell chemotactic and mitogenic activities. These monoclonal antibodies also inhibit the growth of typically less well vascularized human colon cancers in athymic mice and decrease the number of tumors arising from inoculated cells.

Viral expression of a VEGF-binding construct of Flk-1, Flt-1, the mouse KDR receptor homologue, truncated to eliminate the cytoplasmic tyrosine kinase domains but retaining a membrane anchor, virtually abolishes the growth of a transplantable glioblastoma in mice presumably by the dominant negative mechanism of heterodimer formation with membrane spanning endothelial cell VEGF receptors. Embryonic stem cells, which normally grow as solid tumors in nude mice, do not produce detectable tumors if both VEGF alleles are knocked out. Taken together, these data indicate the role of VEGF in the growth of solid tumors. Inhibition of KDR or Flt-1 is implicated in pathological angiogenesis, and these receptors are useful in the treatment of diseases in which angiogenesis is part of the overall pathology, e.g., inflammation, diabetic retinal vascularization, as well as various forms of cancer since tumor growth is known to be dependent on angiogenesis. (Weidner et al., N. Engl. J. Med., 324, pp. 1–8, 1991).

Although similar piperazinyl compounds have been previously reported to be useful as tyrosine kinase inhibitors (see WO 01/17995, published Mar. 15, 2001) a need still exists for forms of the compounds that can be readily administered to patients, especially orally active, soluble forms of 4-[2-(5-cyano-thiazol-2-ylamino)-pyridin-4-ylmethyl]-piperazine-1-carboxylic acid methylamide that have thermal stability upon storage. Accordingly, the identification of polymorphs of 4-[2-(5-cyano-thiazol-2-ylamino)-pyridin-4-ylmethyl]-piperazine-1-carboxylic acid methylamide, which specifically inhibit, regulate and/or modulate the signal transduction of tyrosine kinases, is desirable and is an object of this invention.

SUMMARY OF THE INVENTION

The present invention relates to polymorphs of 4-[2-(5-cyano-thiazol-2-ylamino)-pyridin-4-ylmethyl]-piperazine-1-carboxylic acid methylamide that are capable of inhibiting, modulating and/or regulating signal transduction of both receptor-type and non-receptor type tyrosine kinases.

DETAILED DESCRIPTION OF THE INVENTION

Figure 1:
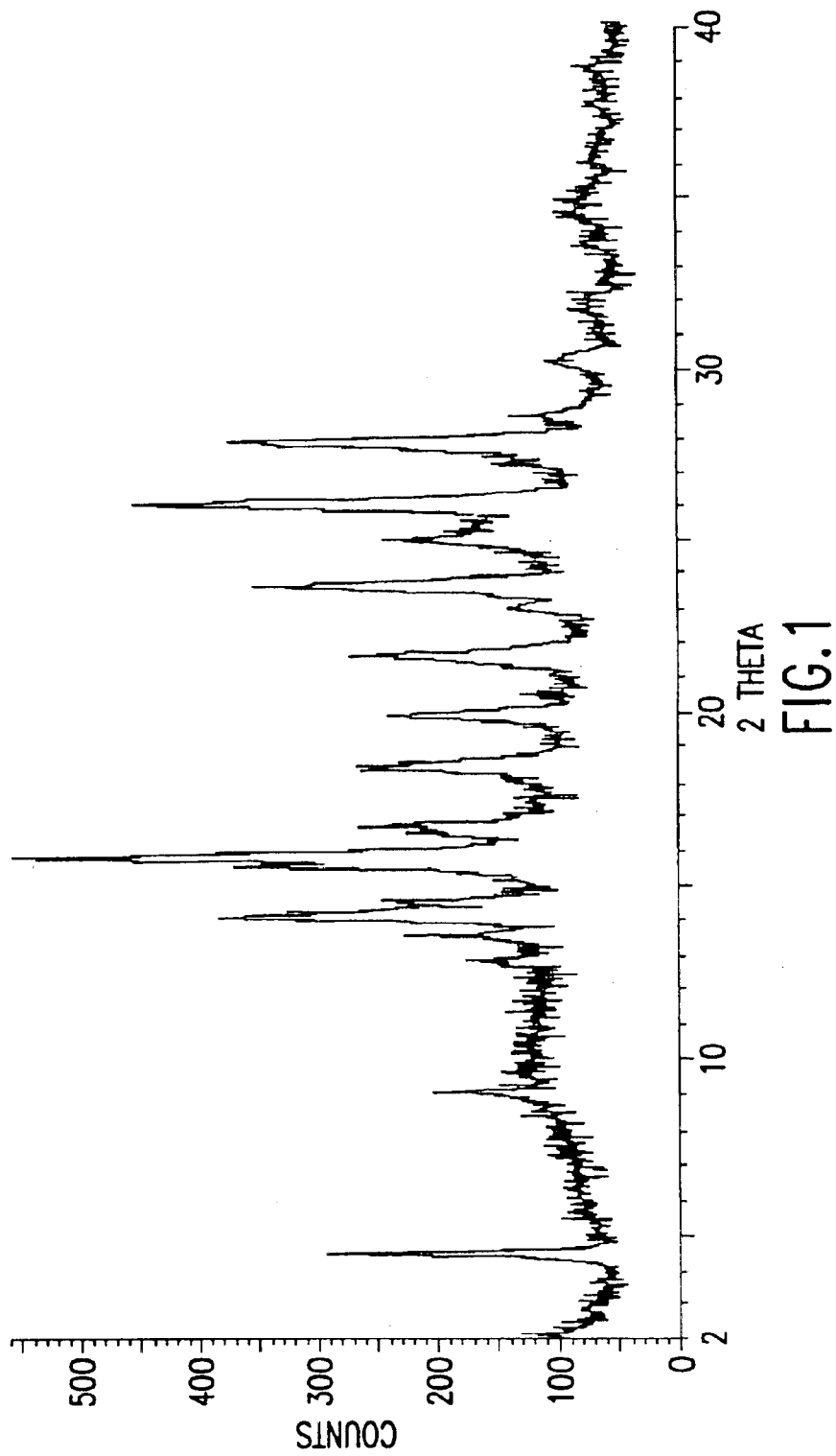
FIG. 1: X-ray powder diffraction pattern of the free base (Form 1) of 4-[2-(5-cyano-thiazol-2-ylamino)-pyridin-4-ylmethyl]-piperazine-1-carboxylic acid methyl amide.

4-[2-(5-cyano-thiazol-2-ylamino)-pyridin-4-ylmethyl]-piperazine-1-carboxylic acid methylamide (Compound 4-4) is an inhibitor of tyrosine kinase signal transduction and, in particular, inhibits the kinase KDR. Two polymorph forms (Forms 1 and 2) of the free base of Compound 4-4 have been observed.

An embodiment of the invention is illustrated by Form 1 of the free base of 4-[2-(5-cyano-thiazol-2-ylamino)-pyridin-4-ylmethyl]-piperazine-1-carboxylic acid methylamide in crystalline form characterized by an X-ray powder diffraction pattern having diffraction angles of: (with an experimental error of about ±0.8°) 4.42, 8.93, 12.69, 13.39, 13.95, 14.44, 15.44, 15.72, 16.60, 18.31, 19.84, 21.55, 22.86, 23.54, 24.87, 25.92, 27.73, and 28.53.

An embodiment of the invention is illustrated by Form 2 of the free base of 4-[2-(5-cyano-thiazol-2-ylamino)-pyridin-4-ylmethyl]-piperazine-1-carboxylic acid methylamide in crystalline form characterized by an X-ray powder diffraction pattern having diffraction angles of: (with an experimental error of about ±0.8°) 4.29, 8.72, 12.35, 13.16, 14.50, 15.05, 15.83, 16.06, 16.44, 16.84, 18.04, 19.73, 21.15, 22.27, 23.41, 24.65, 25.05, 25.57, 26.25, and 27.11.

The polymorphs of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119–1190), and occur as racemates, racemic mixtures, and as individual diastereomers, with all possible isomers and mixtures thereof, including optical isomers, being included in the present invention. In addition, the polymorphs disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

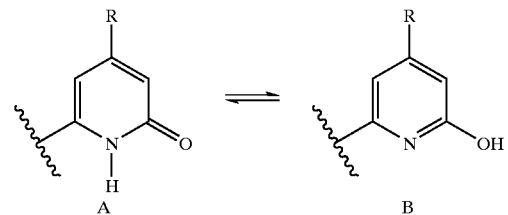

The instantly disclosed polymorphs are inhibitors of tyrosine kinase and are therefore useful to treat or prevent tyrosine kinase-dependent diseases or conditions in mammals.

"Tyrosine kinase-dependent diseases or conditions" refers to pathologic conditions that depend on the activity of one or more tyrosine kinases. Tyrosine kinases either directly or indirectly participate in the signal transduction pathways of a variety of cellular activities including proliferation, adhesion and migration, and differentiation. Diseases associated with tyrosine kinase activities include the proliferation of tumor cells, the pathologic neovascularization that supports solid tumor growth, ocular neovascularization (diabetic retinopathy, age-related macular degeneration, retinal ischemia, macular edema, and the like) and inflammation (psoriasis, rheumatoid arthritis, and the like). In treating such conditions with the instantly claimed polymorphs, the required therapeutic amount will vary according to the specific disease and is readily ascertainable by those skilled in the art. Although both treatment and prevention are contemplated by the scope of the invention, the treatment of these conditions is the preferred use.

Also included within the scope of the claims is a composition which is comprised of a polymorph of the present invention and a pharmaceutically acceptable carrier.

The present invention also encompasses a method of treating or preventing cancer in a mammal in need of such treatment which is comprised of administering to said mammal a therapeutically effective amount of a presently disclosed polymorph. The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

Preferred cancers for treatment are selected from cancers of the brain, genitourinary tract, lymphatic system, stomach, larynx and lung. Another set of preferred forms of cancer are histiocytic lymphoma, lung adenocarcinoma, small cell lung cancers, pancreatic cancer, gioblastomas and breast carcinoma. The utility of angiogenesis inhibitors in the treatment of cancer is known in the literature, see J. Rak et al. *Cancer Research,* 55:4575–4580, 1995, for example. The role of angiogenesis in cancer has been shown in numerous types of cancer and tissues: breast carcinoma (G. Gasparini and A. L. Harris, *J. Clin. Oncol.,* 1995, 13:765–782; M. Toi et al., *Japan. J. Cancer Res.,* 1994, 85:1045–1049); bladder carcinomas (A. J. Dickinson et al., *Br. J. Urol.,* 1994, 74:762–766); colon carcinomas (L. M. Ellis et al., *Surgery,* 1996, 120(5):871–878); and oral cavity tumors (J. K. Williams et al., *Am. J. Surg.,* 1994, 168:373–380).

Also included is a method of treating or preventing a disease in which angiogenesis is implicated, which is comprised of administering to a mammal in need of such treatment a therapeutically effective amount of a polymorph of the instant invention. Such a disease in which angiogenesis is implicated is ocular diseases such as retinal vascularization, diabetic retinopathy, age-related macular degeneration, retinal ischemia, macular edema, and the like.

Tumors which have undergone neovascularization show an increased potential for metastasis. VEGF released from cancer cells enhances metastasis possibly by increasing extravasation at points of adhesion to vascular endothelium. (A. Amirkhosravi et al., *Platelets,* 10:285–292 (1999).) In fact, angiogenesis is essential for tumor growth and metastasis. (S. P. Gunningham, et al., *Can. Research,* 61: 3206–3211 (2001)). The angiogenesis inhibitors disclosed in the present application are therefore also useful to prevent or decrease tumor cell metastasis. Such a use is also contemplated to be within the scope of the present invention.

Further included within the scope of the invention is a method of treating or preventing a disease in which angiogenesis is implicated, which is comprised of administering to a mammal in need of such treatment a therapeutically effective amount of a polymorph of the instant invention. Ocular neovascular diseases are an example of conditions where much of the resulting tissue damage can be attributed to aberrant infiltration of blood vessels in the eye. (see WO 00/30651, published 2 Jun. 2000.) The undesirable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration. Inhibiting the growth of blood vessels by administration of a polymorph of the instant invention would therefore prevent the infiltration of blood vessels and prevent or treat diseases where angiogenesis is implicated, such as ocular diseases like retinal vascularization, diabetic retinopathy, age-related macular degeneration, retinal ischemia, macular edema, and the like.

A method of treating or preventing preeclampsia is also within the scope of the present invention, which comprises administering a therapeutically effective amount of a polymorph of the instant invention. Studies have shown that the action of VEGF on the Flt-1 receptor is pivotal in the pathogenesis of preeclampsia. (*Laboratory Investigation* 79:1101–1111 (September 1999)). Vessels of pregnant women incubated with VEGF exhibit a reduction in endothelium-dependent relaxation similar to that induced by plasma from women with preeclampsia. In the presence of an anti-Flt-1 receptor antibody, however, neither VEGF or plasma from women with preeclampsia reduced the endothelium-dependent relaxation. Therefore the claimed polymorph of the instant invention serve to treat preeclampsia via their action on the tyrosine kinase domain of the Flt-1 receptor.

Also within the scope of the invention is a method of reducing or preventing tissue damage following a cerebral ischemic event which comprises administering a therapeutically effective amount of a polymorph of the instant invention. The claimed polymorph can also be used to reduce or prevent tissue damage which occurs after cerebral ischemic events, such as stroke, by reducing cerebral edema, tissue damage, and reperfusion injury following ischemia. (*Drug News Perspect* 11:265–270 (1998); *J. Clin. Invest.* 104:1613–1620 (1999); *Nature Med* 7:222–227 (2001)).

Also included within the scope of the present invention is a method of treating or preventing inflammatory diseases which comprises administering to a mammal in need of such treatment a therapeutically effective amount of a polymorph of the instant invention. Examples of such inflammatory diseases are rheumatoid arthritis, psoriasis, contact dermatitis, delayed hypersensitivity reactions, and the like. (A. Giatromanolaki et al., *J. Pathol.* 2001; 194:101–108.)

Also included is a method of treating or preventing a tyrosine kinase-dependent disease or condition in a mammal which comprises administering to a mammalian patient in need of such treatment a therapeutically effective amount of a polymorph of the instant invention. The therapeutic amount varies according to the specific disease and is discernable to the skilled artisan without undue experimentation.

A method of treating or preventing retinal vascularization which is comprised of administering to a mammal in need of such treatment a therapeutically effective amount of a polymorph of the instant invention is also encompassed by the present invention. Methods of treating or preventing ocular diseases, such as diabetic. retinopathy, age-related macular degeneration, retinal ischemia and macular edema, are also part of the invention. Also included within the scope of the present invention is a method of treating or preventing inflammatory diseases, such as rheumatoid arthritis, psoriasis, contact dermatitis and delayed hypersensitivity reactions, as well as treatment or prevention of bone associated pathologies selected from osteosarcoma, osteoarthritis, and rickets, also known as oncogenic osteomalacia. (Hasegawa et al., *Skeletal Radiol.,* 28, pp. 41–45, 1999; Gerber et al., *Nature Medicine, Vol.* 5, No. 6, pp. 623–628, June 1999). And since VEGF directly promotes osteoclastic bone resorption through KDR/Flk-1 expressed in mature osteoclasts (FEBS Let. 473:161–164 (2000); *Endocrinology,* 141:1667 (2000)), the instant polymorphs are also useful to treat and prevent conditions related to bone resorption, such as osteoporosis and Paget's disease.

The invention also contemplates the use of the instantly claimed polymorphs in combination with another compound selected from:

1) an estrogen receptor modulator,
2) an androgen receptor modulator,
3) retinoid receptor modulator, 4) a cytotoxic agent, 5) an antiproliferative agent, 6) a prenyl-protein transferase inhibitor, 7) an HMG-CoA reductase inhibitor, 8) an HIV protease inhibitor, 9) a reverse transcriptase inhibitor, and 10) another angiogenesis inhibitor.

Preferred angiogenesis inhibitors are selected from the group consisting of a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combreta-statin A-4, squalamine, 6-O-chloroacetyl-carbonyl)-fumagillol, thalidomide, angiostatin, troponin-1, and an antibody to VEGF. Preferred estrogen receptor modulators are tamoxifen and raloxifene.

Also included in the scope of the claims is a method of treating cancer which comprises administering a therapeutically effective amount of a polymorph of the instant invention in combination with radiation therapy-and/or in combination with a compound selected from:

1) an estrogen receptor modulator, 2) an androgen receptor modulator, 3) retinoid receptor modulator, 4) a cytotoxic agent, 5) an antiproliferative agent, 6) a prenyl-protein transferase inhibitor, 7) an HMG-CoA reductase inhibitor, 8) an HIV protease inhibitor, 9) a reverse transcriptase inhibitor, and 10) another angiogenesis inhibitor.

And yet another embodiment of the invention is a method of treating cancer which comprises administering a therapeutically effective amount of a polymorph of the instant invention in combination with paclitaxel or trastuzumab.

Also within the scope of the invention is a method of reducing or preventing tissue damage following a cerebral ischemic event which comprises administering a therapeutically effective amount of a polymorph of the instant invention.

Some of the abbreviations that may be used in the description of the chemistry and in the Examples include:

| | |
|---|---|
| ACN | Acetonitrile; |
| Ac₂O | Acetic anhydride; |
| AcOH | Acetic acid; |
| AIBN | 2,2'-Azobisisobutyronitrile; |
| BINAP | 2,2'-Bis(diphenylphosphino)-1,1' binaphthyl; |
| Bn | Benzyl; |
| BOC/Boc | tert-Butoxycarbonyl; |
| BSA | Bovine Serum Albumin; |
| CAN | Ceric Ammonium Nitrate; |
| CBz | Carbobenzyloxy; |
| CI | Chemical Ionization; |
| DBA | dibenzanthracene; |
| DBAD | Di-tert-butyl azodicarboxylate; |
| DBU | 1,8-Diazabicyclo[5.4.0]undec-7-ene; |
| DCE | 1,2-Dichloroethane; |
| DEAD | diethylazodicarboxylate; |
| DEM | diethoxymethane; |
| DIAD | diisopropylazodicarboxylate; |
| DIEA | N,N-Diisopropylethylamine; |
| DMAC | N,N-dimethylacetamide; |
| DMAP | 4-Dimethylaminopyridine; |
| DME | 1,2-Dimethoxyethane; |
| DMF | N,N-Dimethylformamide; |
| DMPU | 1,3-Dimethyl-3,4,5,6-tetrahydro-2-(1H)-pyrimidinone; |
| DMSO | Methyl sulfoxide; |
| DPAD | dipiperidineazodicarbonyl; |
| DPPA | Diphenylphosphoryl azide; |
| DTT | Dithiothreitol; |
| EDC | 1-(3-Dimethylaminopropyl)-3-ethyl-carbodiimide-hydrochloride; |
| EDTA | Ethylenediaminetetraacetic acid; |
| ES | Electrospray; |
| ESI | Electrospray ionization; |
| Et₂O | Diethyl ether; |
| Et₃N | Triethylamine; |
| EtOAc | Ethyl acetate; |
| EtOH | Ethanol; |
| FAB | Fast atom bombardment; |
| HEPES | 4-(2-Hydroxyethyl)-1-piperazineethanesulfonic acid; |
| HOAc | Acetic acid; |
| HMTA | Hexamethylenetetramine; |
| HOBT | 1-Hydroxybenzotriazole hydrate; |
| HOOBT | 3-Hydroxy-1,2,2-benzotriazin-4(3H)-one; |
| HPLC | High-performance liquid chromatography; |
| HRMS | High Resolution Mass Spectroscopy; |
| KOtBu | Potassium tert-butoxide; |
| LAH | Lithium aluminum hydride; |
| LCMS | Liquid Chromatography Mass Spectroscopy; |
| MCPBA | m-Chloroperoxybenzoic acid; |
| Me | Methyl; |
| MEK | Methyl ethyl ketone; |
| MeOH | Methanol; |
| MIBK | Methyl isobutyl ketone; |
| Ms | Methanesulfonyl; |
| MS | Mass Spectroscopy; |
| MsCl | Methanesulfonyl chloride; |
| MsOH | methanesulfonic acid; |
| MTBE | tert-butyl methyl ether; |
| n-Bu | n-butyl; |
| n-Bu₃P | Tri-n-butylphosphine; |
| NaHMDS | Sodium bis(trimethylsilyl)amide; |
| NBS | N-Bromosuccinimide; |
| NMP | N-Methyl pyrrolidinone; |
| ODCB | Ortho Dichlorobenzene, or 1,2-dichlorobenzene; |
| Pd(PPh₃)₄ | Palladium tetrakis(triphenylphosphine); |
| Pd₂(dba)₂ | Tris(dibenzylideneacetone)dipalladium (0) |
| Ph | phenyl; |
| PMSF | α-Toluenesulfonyl fluoride; |
| Py or pyr | Pyridine; |
| PYBOP (or PyBOP) | Benzotriazol-1-yloxytripyrrolidinophosphonium hexafluorophosphate; |
| RPLC | Reverse Phase Liquid Chromatography; |
| rt (or RT) | Room Temperature; |
| t-Bu | tert-Butyl; |
| TBAF | Tetrabutylammonium fluoride; |
| TBSCl | tert-Butyldimethylsilyl chloride; |
| TFA | Trifluoroacetic acid; |
| THF | Tetrahydrofuran; |
| TIPS | Triisopropylsilyl; |
| TMEDA | N,N,N',N'-Tetramethylethylenediamine; |
| TMS | Tetramethylsilane; |
| Tr | Trityl; and |
| TsOH | P-Toluenesulfonic acid. |

These and other aspects of the invention will be apparent from the teachings contained herein.

Utility

The polymorphs of the instant invention are useful as pharmaceutical agents for mammals, especially for humans, in the treatment of tyrosine kinase dependent diseases. Such diseases include the proliferation of tumor cells, the pathologic neovascularization (or angiogenesis) that supports solid tumor growth, ocular neovascularization (diabetic retinopathy, age-related macular degeneration, retinal ischemia, macular edema, and the like) and inflammation (psoriasis, rheumatoid arthritis, and the like). Based on pharmacokinetic studies in animals, the presently claimed polymorphs have an unexpectedly superior oral activity profile compared to the corresponding free base and are therefore particularly suited for oral administration. They may, however, be administered via other routes as described herein.

The polymorphs of the instant invention may be administered to patients for use in the treatment of cancer. The instant polymorphs inhibit tumor angiogenesis, thereby affecting the growth of tumors (J. Rak et al. *Cancer Research,* 55:4575–4580, 1995). The anti-angiogenesis properties of the instant polymorphs are also useful in the treatment of certain forms of blindness related to retinal vascularization.

The polymorphs of the instant invention are also useful in the treatment of certain bone-related pathologies, such as osteosarcoma, osteoarthritis, and rickets, also known as oncogenic osteomalacia. (Hasegawa et al., Skeletal Radiol., 28, pp. 41–45, 1999; Gerber et al., Nature Medicine, Vol. 5, No. 6, pp. 623–628, June 1999). And since VEGF directly promotes osteoclastic bone resorption through KDR/Flk-1 expressed in mature osteoclasts (FEBS Let. 473:161–164 (2000); Endocrinology, 141:1667 (2000)), the instant polymorphs are also useful to treat and prevent conditions related to bone resorption, such as osteoporosis and Paget's disease.

The claimed polymorphs can also be used to reduce or prevent tissue damage which occurs after cerebral ischemic events, such as stroke, by reducing cerebral edema, tissue damage, and reperfusion injury following ischemia. (*Drug News Perspect* 11:265–270 (1998); *J. Clin. Invest.* 104:1613–1620 (1999).)

The polymorphs of the instant invention may also be co-administered with other well known therapeutic agents that are selected for their particular usefulness against the condition that is being treated. For example, in the case of bone-related disorders, combinations that would be useful include those with antiresorptive bisphosphonates, such as alendronate and risedronate; integrin blockers (defined further below), such as $\alpha_\nu\beta_3$ antagonists; conjugated estrogens used in hormone replacement therapy, such as PREMPRO®, PREMARIN® and ENDOMETRION®; selective estrogen receptor modulators (SERMs), such as raloxifene, droloxifene, CP-336,156 (Pfizer) and lasofoxifene; cathespin K inhibitors; and ATP proton pump inhibitors.

The instant polymorphs are also useful in combination with known anti-cancer agents. Such known anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds which interfere or inhibit the binding of estrogen to the receptor, regardless of mechanism. Examples of estrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, and N-4-carboxyphenyl retinamide.

"Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-yridine) platinum, benzylguanine, glufosfamide, GPX100, (trans, trans, trans)-bis-mu-(hexane-1,6-diamine)-mu-[diamine-platinum(II)]bis[diamine(chloro) platinum (II)]tetrachloride, diarizidinylspermine, arsenic trioxide, 1-(11-dodecylamino-10-hydroxyundecyl)-3,7-dimethylxanthine, zorubicin, idarubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin.

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) enzene sulfonamide, anhydrovinblastine, N,N-dimethyl-L-valyl-L-valyl-N-methyl-L-valyl-L-prolyl-L-proline-t-butylamide, TDX258, and BMS 188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl] acridine-2-(6H) propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)dione, lurtotecan, 7-[2-(N-isopropylamino)ethyl]-(20S) camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa, 9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl) amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin- 6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl) urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4. 1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820, 850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85–89 (Feb. 5, 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

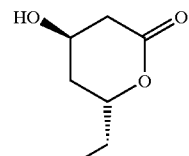
Lactone

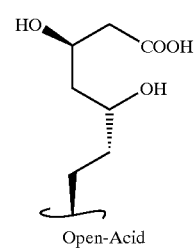
Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (+)-6-[amino(4-chlorophenyl)(1-methyl-1H-imidazol-5-yl)methyl]-4-(3-chlorophenyl)-1-methyl-2(1H)-quinolinone, (−)-6-[amino(4-chlorophenyl)(1-methyl-1H-imidazol-5-yl)methyl]-4-(3-chlorophenyl)-1-methyl-2(1H)-quinolinone, (+)-6-[amino(4-chlorophenyl)(1-methyl-1H-imidazol-5-yl)methyl]-4-(3-chlorophenyl)-1-methyl-2(1H)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)methyl]-2-piperazinone, 5(S)-n-Butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{5-[4-Hydroxymethyl-4-(4-chloropyridin-2-ylmethyl)-piperidine-1-ylmethyl]-2-methylimidazol-1-ylmethyl} benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2']bipyridin-5'-ylmethyl]-3H-imidazol-4-ylmethyl}benzonitrile, 4-{3-[4-(2-Oxo-2H-[1,2'] bipyridin-5'-ylmethyl]-3H-imidazol-4-ylmethyl}benzonitrile, 4-[3-(2-Oxo-1-phenyl-1,2-dihydropyridin-4-ylmethyl)-3H-imidazol-4-ylmethyl}benzonitrile, 18,19-dihydro-19-oxo-5H,17H-6,10:12,16-dimetheno-1H-imidazo[4,3-c][1,11,4]dioxaazacyclo-nonadecine-9-carbonitrile, (±)-19,20-Dihydro-19-oxo-5H-18,21-ethano-12,14-etheno-6,10-metheno-22H-benzo[d]imidazo[4,3-k][1,6,9,12]oxatriazacyclooctadecine-9-carbonitrile, 19,20-dihydro-19-oxo-5H,17H-18,21-ethano-6,10:12,16-dimetheno-22H-imidazo[3,4-h][1,8,11,14]oxatriazacycloeicosine-9-carbonitrile, and (±)-19,20-Dihydro-3-methyl-19-oxo-5H-18,21-ethano-12,14-etheno-6,10-metheno-22H-benzo [d]imidazo[4,3-k][1,6,9,12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394–1401 (1999).

Examples of HIV protease inhibitors include amprenavir, abacavir, CGP-73547, CGP-61755, DMP-450, indinavir, nelfinavir, tipranavir, ritonavir, saquinavir, ABT-378, AG 1776, and BMS-232,632. Examples of reverse transcriptase inhibitors include delaviridine, efavirenz, GS-840, HB Y097, lamivudine, nevirapine, AZT, 3TC, ddC, and ddI.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclo-oxygenase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141–145 (1985)), and antibodies to VEGF (see, Nature Biotechnology, Vol. 17, pp. 963–968 (October 1999); Kim et al., Nature, 362, 841–844 (1993) WO 00/44777; and WO 00/61186).

Other therapeutic agents that modulate or inhibit angiogenesis and may also be used in combination with the polymorphs of the instant invention include agents that modulate or inhibit the coagulation and fibrinolysis systems (see review in Clin. Chem. La. Med. 38:679–692 (2000)). Examples of such agents that modulate or inhibit the coagulation and fibrinolysis pathways include, but are not limited to, heparin (see Thromb. Haemost. 80:10–23 (1998)), low molecular weight heparins and carboxypeptidase U inhibitors (also known as inhibitors of active thrombin activatable fibrinolysis inhibitor [TAFIa]) (see Thrombosis Res. 101:329–354 (2001)). TAFIa inhibitors have been described in U.S. Ser. Nos. 60/310,927 (filed Aug. 8, 2001) and 60/349,925(filed Jan. 18, 2002).

As described above, the combinations with NSAID's are directed to the use of NSAID's which are potent COX-2 inhibiting agents. For purposes of this specification an NSAID is potent if it possess an IC50 for the inhibition of COX-2 of 1 μM or less as measured by the cell or microsomal assay disclosed herein.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by the cell or microsomal assay disclosed hereinunder. Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995 (Celebrex), U.S. Pat. No. 5,633,272, issued May 27, 1997 (Valdecoxib), and U.S. Pat. No. 5,932,598, issued Aug. 3, 1999 (Parecoxib), all of which are hereby incorporated by reference.

Inhibitors of COX-2 that are particularly useful in the instant method of treatment are:

3-phenyl-4-(4-(methylsulfonyl)phenyl)-2-(5H)-furanone; and

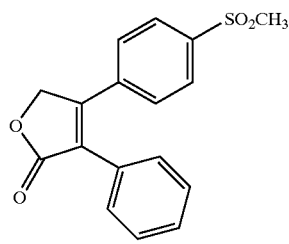

5-chloro-3-(4-methylsulfonyl)phenyl-2-(2-methyl-5-pyridinyl)pyridine;

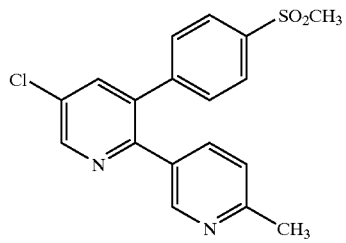

or a pharmaceutically acceptable salt thereof.

General and specific synthetic procedures for the preparation of the COX-2 inhibitor compounds described above are found in U.S. Pat. No. 5,474,995, issued Dec. 12, 1995, U.S. Pat. No. 5,861,419, issued Jan. 19, 1999, and U.S. Pat. No. 6,001,843, issued Dec. 14, 1999, all of which are herein incorporated by reference.

Compounds that have been described as specific inhibitors of COX-2 and are therefore useful in the present invention include, but are not limited to, the following:

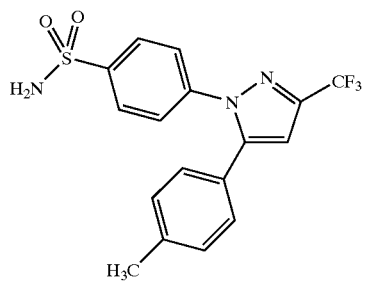

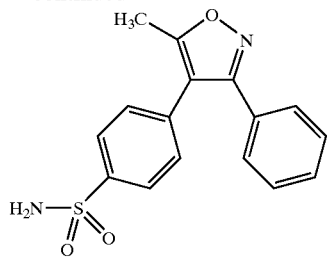

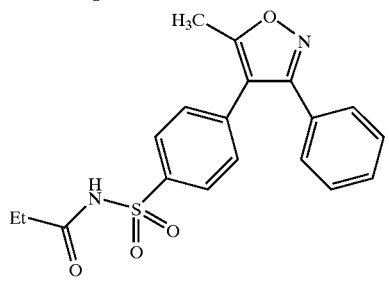

or a pharmaceutically acceptable salt thereof.

Compounds, which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995 (Celebrex), U.S. Pat. No. 5,633,272, issued May 27, 1997 (Valdecoxib), and U.S. Pat. No. 5,932,598, issued Aug. 3, 1999 (Parecoxib).

Compounds which are specific inhibitors of COX-2 and are therefore useful in the present invention, and methods of synthesis thereof, can be found in the following patents, pending applications and publications, which are herein incorporated by reference: U.S. Pat. No. 5,474,995 issued Dec. 12, 1995, U.S. Pat. No. 5,861,419 issued Jan. 19, 1999, U.S. Pat. No. 6,001,843 issued Dec. 14, 1999, U.S. Pat. No. 6,020,343 issued Feb. 1, 2000, U.S. Pat. No. 5,409,944 issued Apr. 25, 1995, U.S. Pat. No. 5,436,265 issued Jul. 25, 1995, U.S. Pat. No. 5,536,752 issued Jul. 16, 1996, U.S. Pat. No. 5,550,142 issued Aug. 27, 1996, U.S. Pat. No. 5,604,260 issued Feb. 18, 1997, U.S. Pat. No. 5,698,584 issued Dec. 16, 1997, and U.S. Pat. No. 5,710,140 issued Jan. 20, 1998.

Other examples of angiogenesis inhibitors include, but are not limited to, endostation, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide,CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the αvβ3 integrin, to compounds which selectively antagonize, inhibit or counteract binding of a physiological ligand to the αvβ5 integrin, to compounds which antagonize, inhibit or counteract binding of a physiological ligand to both the αvβ3 integrin and the αvβ5 integrin, and to compounds which antagonize, inhibit or counteract the activity of the particular integrin(s) expressed on capillary endothelial cells. The term also refers to antagonists of the αvβ6, αvβ8, α1β1, α2β1, α5β1, α6β1 and α6β4 integrins. The term also refers to antagonists of any combination of αvβ3, αvβ5, αvβ6, αvβ8, α1β1, α2β1, α5β1, α6β1 and α6β4 integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl) indolin-2-one, 17-(allylamino)-17-demethoxygeldanamycin, 4-(3-chloro-4-fluorophenylamino)-7-methoxy-6-[3-(4-morpholinyl) propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

The instantly claimed polymorphs are also useful, alone or in combination with platelet fibrinogen receptor (GP IIb/IIIa) antagonists, such as tirofiban, to inhibit metastasis of cancerous cells. Tumor cells can activate platelets largely via thrombin generation. This activation is associated with the release of VEGF. The release of VEGF enhances metastasis by increasing extravasation at points of adhesion to vascular endothelium (Amirkhosravi, *Platelets* 10, 285–292, 1999). Therefore, the present salts can serve to inhibit metastasis, alone or in combination with GP IIb/IIIa) antagonists. Examples of other fibrinogen receptor antagonists include abciximab, eptifibatide, sibrafiban, lamifiban, lotrafiban, cromofiban, and CT50352.

Formulation

The polymorphs of the instant invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The polymorphs can be administered orally or parenterally, including the intravenous, intramuscular, intraperitoneal, subcutaneous, rectal and topical routes of administration.

For oral use of a chemotherapeutic compound according to this invention, the selected polymorph may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

If formulated as a fixed dose, combination products, such as those described hereinabove, employ the polymorphs of this invention within the dosage range described below and the other pharmaceutically active agent(s) within its approved dosage range. Polymorphs of the instant invention may alternatively be used sequentially with known pharmaceutically acceptable agent(s) when a combination formulation is inappropriate.

The term "administration" and variants thereof (e.g., "administering" a compound) in reference to a polymorph of the invention means introducing the polymorph or a prodrug of the polymorph into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the polymorph or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active polymorph, or pharmaceutical agent that elicits the biological or medicinal response in a tissue, system, animal or human that is being sought by a researcher, veterinarian, medical doctor or other clinician.

The present invention also encompasses a pharmaceutical composition useful in the treatment of cancer, comprising the administration of a therapeutically effective amount of the polymorphs of this invention, with or without pharmaceutically acceptable carriers or diluents. Suitable compositions of this invention include aqueous solutions comprising polymorphs of this invention and pharmacologically acceptable carriers, e.g., saline, at a pH level, e.g., 7.4.

When a polymorph according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of a polymorph is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

Assays

The polymorphs of the instant invention described in the Examples were tested by the assays described below and were found to have kinase inhibitory activity. Other assays are known in the literature and could be readily performed by those of skill in the art (see, for example, Dhanabal et al., *Cancer Res.* 59:189–197; Xin et al., *J. Biol. Chem.* 274:9116–9121; Sheu et al., *Anticancer Res.* 18:4435–4441; Ausprunk et al., *Dev. Biol.* 38:237–248; Gimbrone et al., *J. Natl. Cancer Inst.* 52:413–427; Nicosia et al., *In Vitro* 18:538–549).

I. VEGF Receptor Kinase Assay

VEGF receptor kinase activity is measured by incorporation of radio-labeled phosphate into polyglutamic acid, tyrosine, 4:1 (pEY) substrate. The phosphorylated pEY product is trapped onto a filter membrane and the incorporation of radio-labeled phosphate quantified by scintillation counting.

Materials

VEGF Receptor Kinase The intracellular tyrosine kinase domains of human KDR (Terman, B. I. et al. Oncogene (1991) vol. 6, pp. 1677–1683.) and Flt-1 (Shibuya, M. et al. Oncogene (1990) vol. 5, pp. 519–524) were cloned as glutathione S-transferase (GST) gene fusion proteins. This was accomplished by cloning the cytoplasmic domain of the KDR kinase as an in frame fusion at the carboxy terminus of the GST gene. Soluble recombinant GST-kinase domain fusion proteins were expressed in Spodoptera frugiperda (Sf21) insect cells (Invitrogen) using a baculovirus expression vector (pAcG2T, Pharmingen).

The other materials used and their compositions were as follows:

Lysis buffer: 50 mM Tris pH 7.4, 0.5 M NaCl, 5 mM DTT, 1 mM EDTA, 0.5% triton X-100, 10% glycerol, 10 mg/mL of each leupeptin, pepstatin and aprotinin and 1 mM phenylmethylsulfonyl fluoride (all Sigma).

Wash buffer: 50 mM Tris pH 7.4, 0.5 M NaCl, 5 mM DTT, 1 mM EDTA, 0.05% triton X-100, 10% glycerol, 10 mg/mL of each leupeptin, pepstatin and aprotinin and 1 mM phenylmethylsulfonyl fluoride.

Dialysis buffer: 50 mM Tris pH 7.4, 0.5 M NaCl, 5 mM DTT, 1 mM EDTA, 0.05% triton X-100, 50% glycerol, 10 mg/mL of each leupeptin, pepstatin and aprotinin and 1 mM phenylmethylsuflonyl fluoride.

10× reaction buffer: 200 mM Tris, pH 7.4, 1.0 M NaCl, 50 mM $MnCl_2$, 10 mM DTT and 5 mg/mL bovine serum albumin (Sigma).

Enzyme dilution buffer: 50 mM Tris, pH 7.4, 0.1 M NaCl, 1 mM DTT, 10% glycerol, 100 mg/mL BSA.

10× Substrate: 750 μg/mL poly (glutamic acid, tyrosine; 4:1) (Sigma).

Stop solution: 30% trichloroacetic acid, 0.2 M sodium pyrophosphate (both Fisher).

Wash solution: 15% trichloroacetic acid, 0.2 M sodium pyrophosphate.

Filter plates: Millipore #MAFC NOB, GF/C glass fiber 96 well plate.

Method

A. Protein Purification

1. Sf21 cells were infected with recombinant virus at a multiplicity of infection of 5 virus particles/ cell and grown at 27° C. for 48 hours.

2. All steps were performed at 4° C. Infected cells were harvested by centrifugation at 1000×g and lysed at 4° C. for 30 minutes with 1/10 volume of lysis buffer followed by centrifugation at 100,000×g for 1 hour. The supernatant was then passed over a glutathione Sepharose column (Pharmacia) equilibrated in lysis buffer and washed with 5 volumes of the same buffer followed by 5 volumes of wash buffer. Recombinant GST-KDR protein was eluted with wash buffer/10 mM reduced glutathione (Sigma) and dialyzed against dialysis buffer.

B. VEGF Receptor Kinase Assay

1) Add 5 μl of inhibitor or control to the assay in 50% DMSO.

2) Add 35 μl of reaction mix containing 5 μl of 10× reaction buffer, 5 μl 25 mM ATP/10 μCi [$^{33}$P]ATP (Amersham), and 5 μl 10× substrate.

3) Start the reaction by the addition of 10 μl of KDR (25 nM) in enzyme dilution buffer.

4) Mix and incubate at room temperature for 15 minutes.

5) Stop by the addition of 50 μl stop solution.

6) Incubate for 15 minutes at 4° C.

7) Transfer a 90 μl aliquot to filter plate.

8) Aspirate and wash 3 times with wash solution.

9) Add 30 μl of scintillation cocktail, seal plate and count in a Wallac Microbeta scintillation counter.

II. Human Umbilical Vein Endothelial Cell Mitogenesis Assay

Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H] thymidine into cellular DNA.

Materials

HUVECs: HUVECs frozen as primary culture isolates are obtained from Clonetics Corp. Cells are maintained in Endothelial Growth Medium (EGM; Clonetics) and are used for mitogenic assays described in passages 3–7 below.

Culture Plates: NUNCLON 96-well polystyrene tissue culture plates (NUNC #167008).

Assay Medium: Dulbecco's modification of Eagle's medium containing 1 g/mL glucose (low-glucose DMEM; Mediatech) plus 10% (v/v) fetal bovine serum (Clonetics).

Test Compounds: Working stocks of test compounds are diluted serially in 100% dimethylsulfoxide (DMSO) to 400-fold greater than their desired final concentrations. Final dilutions to 1× concentration are made directly into Assay Medium immediately prior to addition to cells.

10× Growth Factors: Solutions of human $VEGF_{165}$ (500 ng/mL; R&D Systems) and bFGF (10 ng/mL; R&D Systems) are prepared in Assay Medium.

10× [$^3$H]Thymidine: [Methyl-$^3$H]thymidine (20 Ci/mmol; Dupont-NEN) is diluted to 80 μCi/mL in low-glucose DMEM.

Cell Wash Medium: Hank's balanced salt solution (Mediatech) containing 1 mg/mL bovine serum albumin (Boehringer-Mannheim).

Cell Lysis Solution: 1 N NaOH, 2% (w/v) $Na_2CO_3$.

Method

1. HUVEC monolayers maintained in EGM are harvested by trypsinization and plated at a density of 4000 cells per 100 μL Assay Medium per well in 96-well plates. Cells are growth-arrested for 24 hours at 37° C. in a humidified atmosphere containing 5% $CO_2$.

2. Growth-arrest medium is replaced by 100 μL Assay Medium containing either vehicle (0.25% [v/v] DMSO) or the desired final concentration of test compound. All determinations are performed in triplicate. Cells are then incubated at 37° C. with 5% $CO_2$ for 2 hours to allow test compounds to enter cells.

3. After the 2-hour pretreatment period, cells are stimulated by addition of 10 μL/well of either Assay Medium, 10× VEGF solution or 10× bFGF solution. Cells are then incubated at 37° C. and 5% $CO_2$.

4. After 24 hours in the presence of growth factors, 10× [$^3$H]thymidine (10 μL/well) is added.

5. Three days after addition of [$^3$H]thymidine, medium is removed by aspiration, and cells are washed twice with Cell Wash Medium (400 μL/well followed by 200 μL/well). The washed, adherent cells are then solubilized by addition of Cell Lysis Solution (100 μL/well) and warming to 37° C. for 30 minutes. Cell lysates are transferred to 7-mL glass scintillation vials containing 150 μL of water. Scintillation cocktail (5 mL/vial) is added, and cell-associated radioactivity is determined by liquid scintillation spectroscopy.

Based upon the foregoing assays the polymorphs of the instant invention are inhibitors of VEGF and thus are useful for the inhibition of angiogenesis, such as in the treatment of ocular disease, e.g., diabetic retinopathy and in the treatment of cancers, e.g., solid tumors. The instant polymorphs inhibit VEGF-stimulated mitogenesis of human vascular endothelial cells in culture with $IC_{50}$ values between 0.01–5.0 μM. These polymorphs may also show selectivity over related tyrosine kinases (e.g., FGFR1 and the Src family; for relationship between Src kinases and VEGFR kinases, see Eliceiri et al., Molecular Cell, Vol. 4, pp. 915–924, December 1999).

III. FLT-1 Kinase Assay

Flt-1 was expressed as a GST fusion to the Flt-1 kinase domain and was expressed in baculovirus/insect cells. The following protocol was employed to assay compounds for Flt-1 kinase inhibitory activity:

1) Inhibitors were diluted to account for the final dilution in the assay, 1:20.
2) The appropriate amount of reaction mix was prepared at room temperature:
   10× Buffer (20 mM Tris pH 7.4/0.1 M NaCl/1 mM DTT final)
   0.1M $MnCl_2$ (5 mM final)
   pEY substrate (75 μg/mL)
   ATP/[$^{33}$P]ATP (2.5 μM/1 μCi final)
   BSA (500 μg/mL final).
3) 5 μL of the diluted inhibitor was added to the reaction mix. (Final volume of 5 μL in 50% DMSO). To the positive control wells, blank DMSO (50%) was added.
4) 35 μL of the reaction mix was added to each well of a 96 well plate.
5) Enzyme was diluted into enzyme dilution buffer (kept at 4° C.).
6) 10 μL of the diluted enzyme was added to each well and mix (5 nM final). To the negative control wells, 10 μL 0.5 M EDTA was added per well instead (final 100 mM).
7) Incubation was then carried out at room temperature for 30 minutes.
8) Stopped by the addition of an equal volume (50 μL) of 30% TCA/0.1M Na pyrophosphate.
9) Incubation was then carried out for 15 minutes to allow precipitation.
10) Transfered to Millipore filter plate.
11) Washed 3× with 15% TCA/0.1M Na pyrophosphate (125 μL per wash).
12) Allowed to dry under vacuum for 2–3 minutes.
13) Dryed in hood for about 20 minutes.
14) Assembled Wallac Millipore adapter and added 50 μL of scintillant to each well and counted.

IV. FLT-3 Kinase Assay

Flt-3 was expressed as a GST fusion to the Flt-3 kinase domain, and was expressed in baculovirus/insect cells. The following protocol was employed to assay compounds for Flt-3 kinase inhibitory activity:

1) Dilute inhibitors (account for the final dilution into the assay, 1:20)
2) Prepare the appropriate amount of reaction mix at room temperature.
   10× Buffer (20 mM Tris pH 7.4/0.1 M NaCl/1 mM DTT final)
   0.1M $MnCl_2$ (SmM final)
   pEY substrate (75 μg/mL)
   ATP/[$^{33}$P]ATP (0.5 μM/L μCi final)
   BSA (500 μg/mL final)

3) Add 5 μL of the diluted inhibitor to the reaction mix. (Final volume of 5 μL in 50% DMSO). Positive control wells—add blank DMSO (50%).
4) Add 35 μL of the reaction mix to each well of a 96 well plate.
5) Dilute enzyme into enzyme dilution buffer (keep at 4° C.).
6) Add 10 μL of the diluted enzyme to each well and mix (5–10 nM final). Negative control wells—add 10 μL 0.5 M EDTA per well instead (final 100 mM)
7) Incubate at room temperature for 60 minutes.
8) Stop by the addition of an equal volume (50 μL) of 30% TCA/0.1M Na pyrophosphate.
9) Incubate for 15 minutes to allow precipitation.
10) Transfer to Millipore filter plate.
11) Wash 3× with 15% TCA/0.1M Na pyrophosphate (125 μL per wash).
12) Allow to dry under vacuum for 2–3 minutes.
13) Dry in hood for about 20 minutes.
14) Assemble Wallac Millipore adapter and add 50 μL of scintillant to each well and count.

EXAMPLES

Examples provided are intended to assist in a further understanding of the invention. Particular materials employed, species and conditions are intended to be further illustrative of the invention and not limiting of the reasonable scope thereof.

The free bases used to prepare the polymorphs of this invention may be obtained by employing the procedures described below, as well as those described in WO 01/17995, published Mar. 15, 2001, hereby incorporated by reference. In addition, other procedures may be used such as standard manipulations of reactions that are known in the literature.

HPLC Methods Used:

| HPLC Analysis: | Isocratic method (for solubility studies) |
|---|---|
| Analysis Method (HPLC): | Chromatographic Conditions |
| Column: | BDS HYPESIL, C18 (250 mm × 46 mm), 5 μm particle size |
| Column Temperature: | ambient |
| Detector: | 230 nm (UV wavelength) |
| Column Temp. | Ambient |
| Flow Rate: | 1.0 mL/min |
| Injection Volume: | 20 μL |
| Mobile Phase: | A) 0.1% Phosphoric Acid |
| | B) 100% Acetonitrile |
| Diluent: | 50% Acetonitrile-DI water |
| Gradient Profile: | (A/B) starts from (60/40) and stays at (60/40) for 10 minutes. |
| Run Time: | 10 minutes |

SCHEME 1

Synthesis of 2-chloro-thiazole-5-carbonitrile (1–2)

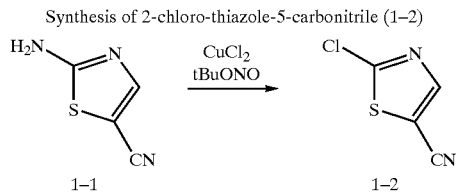

A flame dried round bottom flask under $N_2$ was charged with 150 mL anhydrous MeCN. $CuCl_2$ (12.9 g, 95.9 mmol, 1.2 equiv) was added and the reaction was maintained in a room temperature bath. tert-Butylnitrite (14.3 mL, 120 mmol, 1.5 equiv) was added gradually over 10 minutes. After 10 minutes, 2-amino-thiazole-5-carbonitrile (1—1, 10.0 g, 79.9 mmol) was added as a solid gradually. The reaction was stirred at room temperature for 4 hours. The reaction was poured into 400 mL 0.5M HCl (aq). The mixture was extracted 3× with EtOAc. The organic phases were dried over $Na_2SO_4$, filtered and concentrated to afford pure desired product. $^1$H NMR ($CDC_{13}$) δ 8.04 (s).

SCHEME 2

Syntheis of 4-(t-butyl-dimethyl-silanyloxymethyl)-pyridin-2-ylamine (2–5)

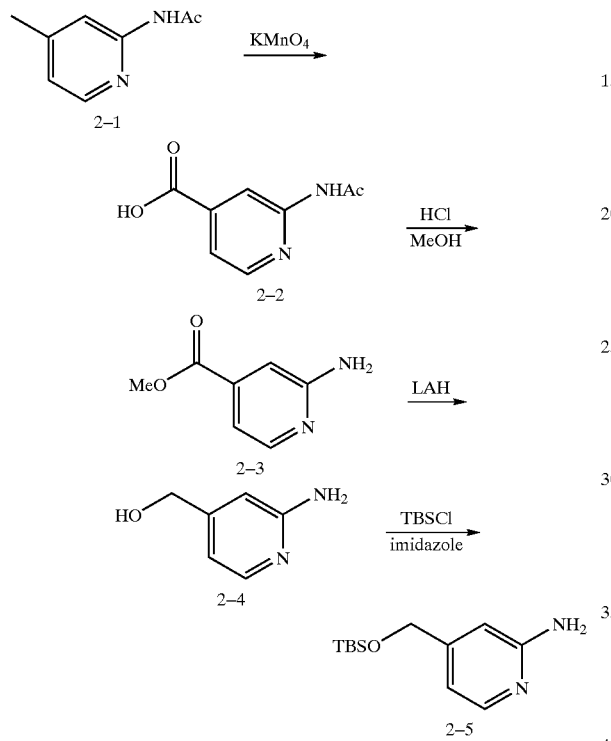

2-Acetylamino-isonicotinic acid (2-2)

N-(4-Methyl-pyridin-2-yl)-acetamide, 70 g (466 mmol) was stirred in 400 mL water. The mixture was warmed to 80° C. $KMnO_4$ (368 g, 2.33 mol, 5 equiv) was added dissolved in water over 45 minutes. The solution was heated to reflux for 3 hours. The reaction was then cooled and filtered. The filtrate was concentrated in vacuo to afford the desired product. $^1$H NMR ($CD_3OD$) δ 8.62 (s, 1H), 8.42 (d, 1H, J=5.1 Hz), 7.59 (dd, 1H, J=5.1 Hz), 2.19 (s, 3H).

2-Amino-isonicotinic acid methyl ester (2-3)

2-Acetylamino-isonicotinic acid (3.10 g, 17.2 mmol) was stirred in 35 mL MeOH at 0° C. HCl (g) was bubbled through the solution for 10 minutes and then the reaction was heated to reflux. After 16 hours the reaction was concentrated in vacuo. The residue was diluted with water and the pH was adjusted to 7 with $Na_2CO_3$ (s). A white precipitate formed which was filtered to afford a portion of pure desired product. The aqueous phase was extracted three times with 95:5 dichloromethane (DCM)/nBuOH. The organic phases were dried over $Na_2SO_4$, filtered and concentrated to afford more of the pure product as a white solid. $^1$H NMR ($CDCl_3$) δ 8.19 (d, 1H, J=5.3 Hz), 7.17 (dd, 1H, J=1.4, 5.3 Hz), 7.07 (d, 1H, J=1.3 Hz), 4.64 (bs, 2H), 3.92 (s, 3H). MS [M+H]+=153.0.

(2-Amino-pyridin-4-yl)-methanol (2-4)

2-Amino-isonicotinic acid methyl ester (6.0 g, 39.4 mmol) was dissolved in 80 mL anhydrous THF in a flame dried round bottom flask under nitrogen gas. The solution was cooled to −45° C. and LAH (39.4 mL, 1M in THF) was added slowly. The reaction was allowed to warm to 0° C. and was quenched by the addition of 15 mL of 1M NaOH (aq). The solution was filtered and the solid was washed with THF. The filtrate was concentrated to afford the pure product. $^1$H NMR (DMSO-$d_6$) δ 7.79 (d, 1H, J=5.2 Hz), 6.41 (s, 1H), 6.38 (d, 1H, J=5.9 Hz), 5.79 (bs, 2H), 5.19 (t, 2H, J=5.7), 4.35 (d, 2H, J=5.6 Hz).

4-(tert-Butyl-dimethyl-silanyloxymethyl)-pyridin-2-ylamine (2-5)

(2-Amino-pyridin-4-yl)-methanol (4.68 g, 37.7 mmol) was dissolved in 40 mL anhydrous DMF under $N_2$. Imidazole (2.57 g, 37.7 mmol, 1 equiv) was added followed by the addition of TBSCl (5.68 g, 37.7 mmol, 1 equiv). After 2 hours the reaction was quenched by the addition of water. A precipitate formed which was filtered to afford pure desired product. The aqueous filtrate was extract 3× with EtOAc. The organic phases were dried over $Na_2SO_4$, filtered and concentrated to afford additional impure material. $^1$H NMR ($CDCl_3$) δ 7.99 (d, 1H, J=5.8 Hz), 6.57 (d, 1H, J=5.1 Hz), 6.51 (s, 1H), 4.64 (s, 2H), 4.40 (bs, 2H), 0.95 (s, 9H), 0.11 (s, 6H).

SCHEME 3

Synthesis of 2-(4-chloromethyl-pyridin-2-ylamino)-thiazole-5-carbonitrile (3–3)

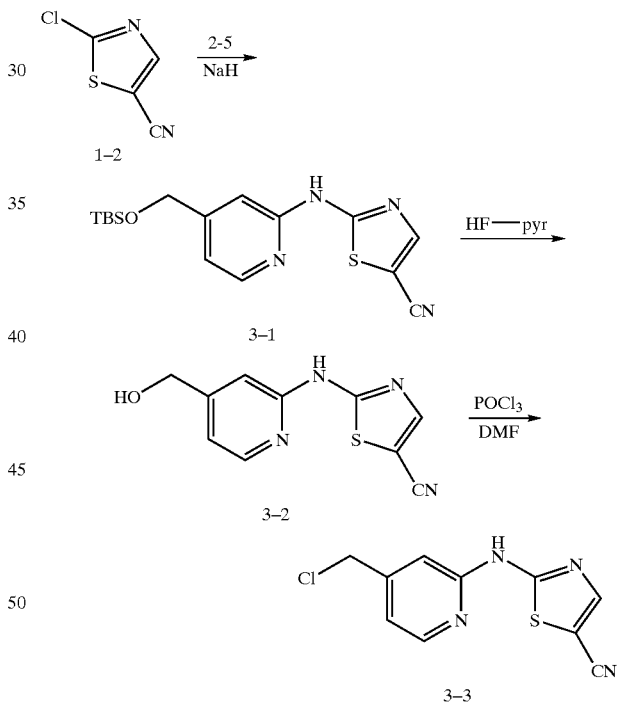

2-[4-(tert-Butyl-dimethyl-silanyloxymethyl)-pyridin-2-ylamino]-thiazole-5-carbonitrile (3-1)

4-(tert-Butyl-dimethyl-silanyloxymethyl)-pyridin-2-ylamine (2-5, 5.94 g, 24.9 mmol) was dissolved in 50 mL anhydrous tetrahydrofuran (THF) under $N_2$. NaH (60% suspension, 2.99 g, 74.8 mmol, 3 equiv) was added (vigorous bubbling occurred) and the resulting mixture was stirred for 15 minutes. 2-Chloro-thiazole-5-carbonitrile (1-2, 4.32 g, 29.9 mmol) was added and the reaction was heated to reflux. After 2 hours the reaction was cooled and was quenched by the addition of water. The THF was removed in vacuo and the resulting aqueous solution was adjusted to pH=7 by the addition of 1M HCl (aq). The resulting precipitate was filtered and washed with water to provide reasonably pure product. $^1$H NMR (CDCl$_3$) δ 10.32 (bs, 1H), 8.33 (d, 1H, J=5.3 Hz), 7.99 (s, 1H), 6.96 (s, 1H), 6.91 (d, 1H, J=5.3 Hz), 4.78 (s, 2H), 0.98 (s, 9H), 0.16 (s, 6H).

2-(4-Hydroxymethyl-pyridin-2-ylamino)-thiazole-5-carbonitrile (3-2)

2-[4-(tert-Butyl-dimethyl-silanyloxymethyl)-pyridin-2-ylamino]-thiazole-5-carbonitrile (1.30 g, 3.75 mmol) was dissolved in 10 mL anh THF. Hydrogen-fluoride (Aldrich, 5.0 mL) was added and the reaction was stirred for 20 minutes. The bulk of the solvent was removed in vacuo and the resulting residue was diluted with half-saturated NaHCO$_3$ (aq). A precipitate formed which was filtered and washed with water to afford the titled compound. $^1$H NMR (DMSO-d$_6$) δ12.23 (bs, 1H), 8.30 (d, 1H, J=5.3 Hz), 8.26 (s, 1H), 7.15 (s, 1H), 6.99 (d, 1H, J=5.3 Hz), 5.49 (t, 1H, J=5.7 Hz) 4.54 (d, 2H, J=5.7 Hz).

2-(4-Chloromethyl-pyridin-2-ylamino)-thiazole-5-carbonitrile (3-3)

2-(4-Hydroxymethyl-pyridin-2-ylamino)-thiazole-5-carbonitrile (0.883 g, 3.80 mmol) was stirred in anhydrous CH$_2$Cl$_2$ (12 mL) under N$_2$. Dimethylformamide (0.354 mL, 3.80 mmol, 1 equiv) was added followed by the addition of phosphorous oxychloride (0.294 mL, 3.80 mmol). After 4 hours the reaction was concentrated and quenched by the addition of saturated NaHCO$_3$ (aq). A precipitate formed which was filtered and washed with water to provide the titled compound. $^1$H NMR (DMSO-d$_6$) δ 12.35 (bs, 1H), 8.40 (d, 1H, J=5.3 Hz), 8.28 (s, 1H), 7.20 (s, 1H), 7.12 (d, 1H, J=5.3 Hz), 4.82 (s, 2H).

SCHEME 4

Synthesis of 4-[2-(5-cyano-thiazol-2-ylamino)-pyridin-4-ylmethyl]-piperazine-1-carboxylic acid methylamide (4-4)

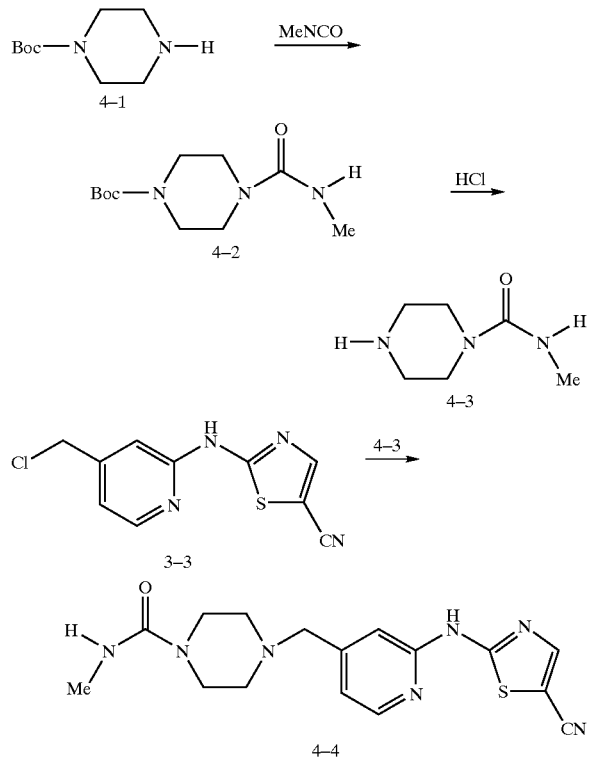

To a solution of Boc-piperazine, 4-1, in CH$_2$Cl$_2$ (200 mL) was added 6.74 g (1 equiv) methylisocyanate in CH$_2$Cl$_2$ (50 mL). The reaction mixture was stirred at room temperature for 6 hours and another 0.25 eq (1.69 g) of methylisocyanate was added. The reaction mixture was then stirred at room temperature overnight. The reaction was subsequently quenched with water (75 mL) and extracted with CH$_2$Cl$_2$ (3×50 mL). The combined organics were dried over Na$_2$SO$_4$, filtered, and concentrated to afford 4-2 as a white solid. $^1$H NMR(CDCl$_3$) δ 4.44 (bs, 1H), 3.48–3.33 (m, 8H), 2.82 (d, 3H, J=4.58), 1.47 (s, 9H).

To a solution of 4-2 in CH$_2$Cl$_2$ at 0° C. was added excess 4.0M HCl (101.5 mL, 406 mmol, 3.5 equiv) in dioxane. The reaction mixture was allowed to warm to room temperature and was stirred for 4 hours. The mixture was then concentrated to afford 1-[(methylamino)carbonyl]piperazin-4-ium chloride, the HCl salt of 4-3, as an off white solid. $^1$H NMR (DMSO-d$_6$) δ9.28 (bs, 1H), 7.94 (bs, 1H), 3.52 (m, 4H), 3.01 (m, 4H), 2.57 (s, 3H).

2-(4-Chloromethyl-pyridin-2-ylamino)-thiazole-5-carbonitrile 3-3 (8.00 g, 31.9 mmol) was stirred in 60 mL DMSO. 1-[(Methylamino)carbonyl]piperazin-4-ium chloride (11.5 g, 63.8 mmol) was added, followed by addition of triethylamine (13.34 mL, 95.7 mmol). The reaction was allowed to stir at room temperature for 15 hours, at which time an additional 2.00 g piperazine hydrochloride (11.1 mmol) was added. No further progress was observed so the reaction was warmed to 45° C. but there was still no further progress. The reaction was cooled to room temperature. An additional 6.6 mL Et$_3$N (48 mmol) was then added. After an additional hour, the reaction was diluted with 300 mL water. The resulting precipitate was filtered, washed with water and air dried. The solid was purified by flash chromatography (eluted with 92:8 DCM/MeOH) to afford the product 4-4. $^1$H NMR (DMSO-d$_6$) δ 12.20 (bs, 1H), 8.32 (d, 1H, J=5.49 Hz), 8.26 (s, 1H), 7.13 (s, 1H), 7.03 (d, 1H, J=5.19 Hz), 6.42 (bd, 1H, J=4.27 Hz), 3.52 (s, 2H), 3.29 (m, 4H), 2.51 (d, 3H, J=4.27 Hz), 2.33 (m, 4H). [M+H]+=358.1443.

SCHEME 5

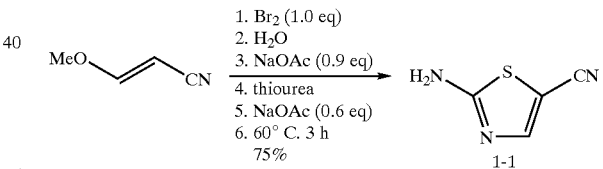

Bromine (2.88 Kg, 18.0 mole) is added to a solution of 3-methoxyacrylonitrile (1.50 Kg, 18.0 mole, mixture of cis-/trans-isomers) in acetonitrile (3.00 L) at 5–10° C. The mixture is aged for 20 minutes, then pre-cooled water (about 5° C., 12.0 L) is added and vigorous stirred for 1 hour.

NaOAc.3H$_2$O, (2.21 Kg, 16.2 mole, 0.90 equiv.) is added and stirred for 15 minutes and then thiourea (1.51 Kg, 19.80 mole, 1.10 equiv.) is added (endothermic dissolution followed by about 10–15° C. exotherm in about 0.5 h). The mixture is aged at 15° C. for 1.5 hour, then more NaOAc.3H$_2$O (1.47 Kg, 0.60 equiv.) is added. It is slowly heated to 60° C. in 1 hour and aged for 3 hours at 60° C. then cooled to 10° C.

NaOH (10 N, 1.13 L, 0.625 equiv.) is added to adjust the pH to 3.8–4.0. After aging for 1 hour, the product is filtered and washed with water (11.5 L). Drying give 1.86 Kg of the crude aminothiazole as a brown solid.

The crude product is dissolved into acetone (35 L) at 50° C. and treated with Darco KB-B (380 g) for 2 hours. It is filtered through a Solka-Floc pad and then rinsed with acetone (5 L). The filtrate is concentrated in vacuo to about 7 L(about 5 L residue acetone). Heptane (10 L) is added in 0.5 hour and the slurry is aged for 1 hour. The product is filtered and the filter cake is washed with 2/1 heptane/acetone (6 L). Drying at rt affords 1.72 Kg of the aminothiazole as a pinkish solid.

HPLC conditions: Ace-C8 4.6×250 mm column; linear gradient: 5–80% MeCN in 12 minutes, 0.1% $H_3PO_4$ in the aqueous mobile phase; Flow rate: 1.50 ml/min; UV detection at 220 nm.

SCHEME 6

Preparation of 9,9-dimethyl-4,5-bis(diphenylphosphino)xanthene, Xantphos

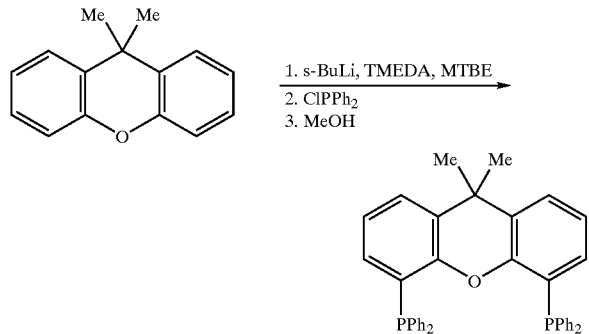

To a 1 L RBF are added MTBE (500 mL), 9,9-dimethylxanthene (26.65 g) and TMEDA (30.6 g). After degassing the solution, s-BuLi (155 g, 1.3 M in cyclohexane) is cannulated into a dropping funnel and then slowly added over 30 min while maintaining the batch temperature at 10–20° C. The mixture is then aged for 16 h at room temperature. $Ph_2PCl$ is added slowly via a dropping funnel while maintain the mildly exothermic reaction at 10–20° C.

Approximately 60% of the $Ph_2PCl$ (30 mL) is added in 0.5 hour. The mixture is aged for 15 minutes before addition of the remaining $Ph_2PCl$. After aged for 5.5 h at room temperature, the reaction is quenched with MeOH (2.0 mL). The product is filtered and the slightly yellow solid is washed consecutively with MeOH (200 mL), water (200 mL), MeOH (200 mL) and MTBE (200 mL) and dried to give an off-white solid as product.

SCHEME 7

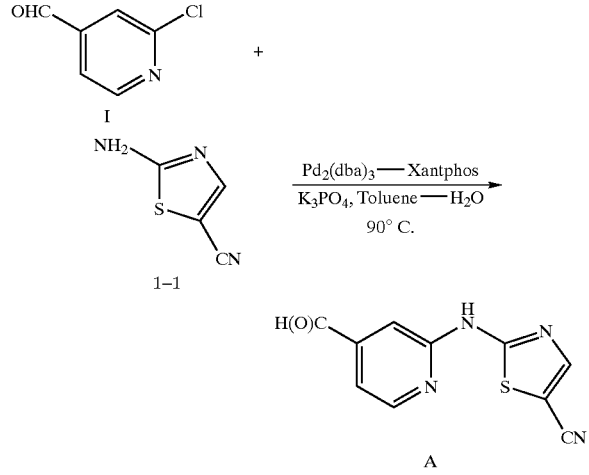

A slurry of 2-chloro-4-formylpyridine (1.49 Kg, 10.5 mole, 1.05 equiv), 2-aminothiazole (1.27 Kg, 10.0 mole, 1.0 equiv), $K_3PO_4$ (2.34 Kg, 11.0 mole, 1.1 equiv) in toluene (20 L) is degassed by two vacuum/nitrogen cycles. $Pd_2(dba)_3$ (114.5 g, 0.125 mmol, 2.5 mol % Pd) and Xantphos (159 g, 0.275 mole, 2.75 mol %) are then added and the mixture is degassed by one vacuum/nitrogen cycle followed by bubbling nitrogen through the slurry for 10 minutes. The mixture is heated to 60° C. and degassed water (90 mL, 5.0 mole, 0.5 equiv) was added over 5 minutes. The mixture is then heated to 90° C. and aged for 8 h.

It is cooled to rt and filtered. The filter cake is washed with toluene (20 L) until very little DBA is observed in the wash. DMAc (24 L) is added to the filter cake to dissolve the product. The insoluble is filtered off and washed with more DMAc (6 L). The filtrate is acidified with concentrate HCl (110 mL) to pH 2.7. Water (3 L) is added and the mixture is concentrated at 40–50° C. under vacuum to remove most of the residual toluene by azeotropic distillation. More water (3×1 L) is added as the distillation progress.

The mixture is seeded and then water (13 L) is added at a rate of about 1.3 L/h. The product is filtered and washed with 5/4 DMAc/water (4.0 L×2), water (4.0 L), acetone (4 L×2), and then oven dried at 40C. under vacuum (100 mmHg) with nitrogen sweep to give the product.

SCHEME 8

Preparation of N-benzyl-N'-methylaminocarbonylpiperazine dihydrate

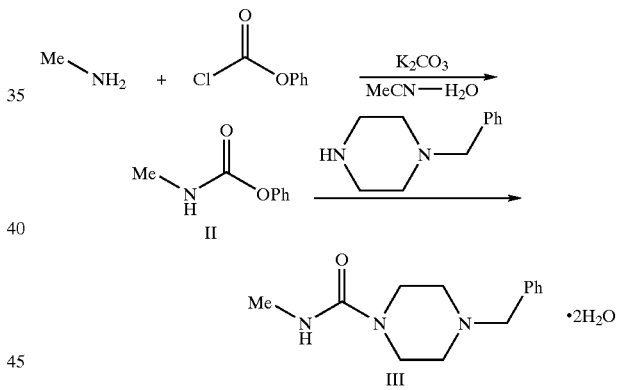

To a 50-L 3-neck RBF is added $H_2O$ (6.0 L) followed by $K_2CO_3$ (4.56 Kg) with stirring. It is cooled to 10° C. Acetonitrile (12 L) and methylamine (40 wt % in water, 1.40 Kg) are added and the mixture is cooled to 0–5° C. Phenyl chloroformate (2.59 Kg) is then added as quickly as possible while maintaining the exothermic reaction at <15° C. 1-Benzylpiperazine is added 15 min after addition of phenyl chloroformate and the biphasic mixture is heated to 70° C. After aging for 1 h at 70° C., the reaction mixture was concentrated under vacuum to remove most of the MeCN.

NaOH (7.5 L 5 N NaOH) is added and the mixture is seeded. The suspension is then cooled to rt and aged for 1 hour. The product is filtered and the filter cake is washed with cold NaOH (0.5 N aq, 4 L×2) and then ice-cold water (4 L×2). It is purified by recrystallization from toluene (15 L) to remove any dibenzylpiperazine impurity. NaOH is used to remove phenol.

SCHEME 9

Preparation of N-methylaminocarbonylpiperazine hydrochloride

HCl (74 mL 12 N, 0.10 eq) is added to MeOH (7 L) and then piperazine urea 1 (2.69 Kg, 10.0 mol) is added. The mixture is hydrogenated using 5% Pd/C (180 g) under 40 psi of hydrogen pressure at 40° C. for 18 h. Pd/C is slurried in MeOH (1 L) and transferred by vacuum. The SM container is rinsed with MeOH (1 L).

After confirming the completion of the reaction, the mixture is filtered through a pad of Solka-Floc and washed with MeOH (2 L) then IPA (4 L). The colorless solution is concentrated to about 5–6 L at about 40° C. under vacuum. IPA (5 L) is added followed by HCl (12 N aq, 0.767 L, 0.92 eq) until the pH of the solution becomes about 3. The mixture is then concentrated under vacuum and flushed with more IPA (5+5 L) to a final volume of 6 L. KF of the supernatant should be <1 w % water. It is then aged at 15° C. for 5 h.

The resulting white crystals are filtered and washed with IPA (4 L). It is then dried in a vacuum oven at 40° C. with slow nitrogen sweep to give product 2.

SCHEME 10

To a slurry of the pyridine aldehyde (2.19 Kg, 94.5 w %, 9.00 mole) and the piperazine urea HCL salt (1.79 Kg, 9.90 mmol) in DMAc (13.5 L) is added Et$_3$N (1.00 Kg, 9.90 mole) followed by acetic acid (2.16 Kg, 36.0 mole) with cooling (15° C). After aging for 0.5 h, NaBH(OAc)$_3$ (2.29 Kg, 10.8 mole) is added in 8 portions (25 minutes/portion).

The mixture is stirred for 1 hour and the completion of the reaction confirmed by HPLC. Water (6.8 L) is added slowly (14 h) to complete the crystallization. Seed with monohydrate of the free base after about 1–2 L of water has been added.

The product is filtered after aging for 3 hours and the filter cake washed with 3/2 DMAc/water (6.7 L), then 1/1 acetone/water (6 L) then acetone (2×4 L). Oven drying at 40 C. with slow nitrogen sweep afforded the free base of Compound 4-4.

The structure of the free base of 4-4 is shown below:

Crystalline Forms 1 and 2 of the free base of 4-4

The free base form of 4-4 has the molecular formula $C_{16}H_{19}N_7OS$ and a molecular weight of 357.44.

Microscopic Characteristics

Microscopic evaluation shows irregularly shaped particles of approximately 50–100 microns, which are birefringent under polarized light.

X-Ray Powder Diffraction (XRPD)

Figure 2:
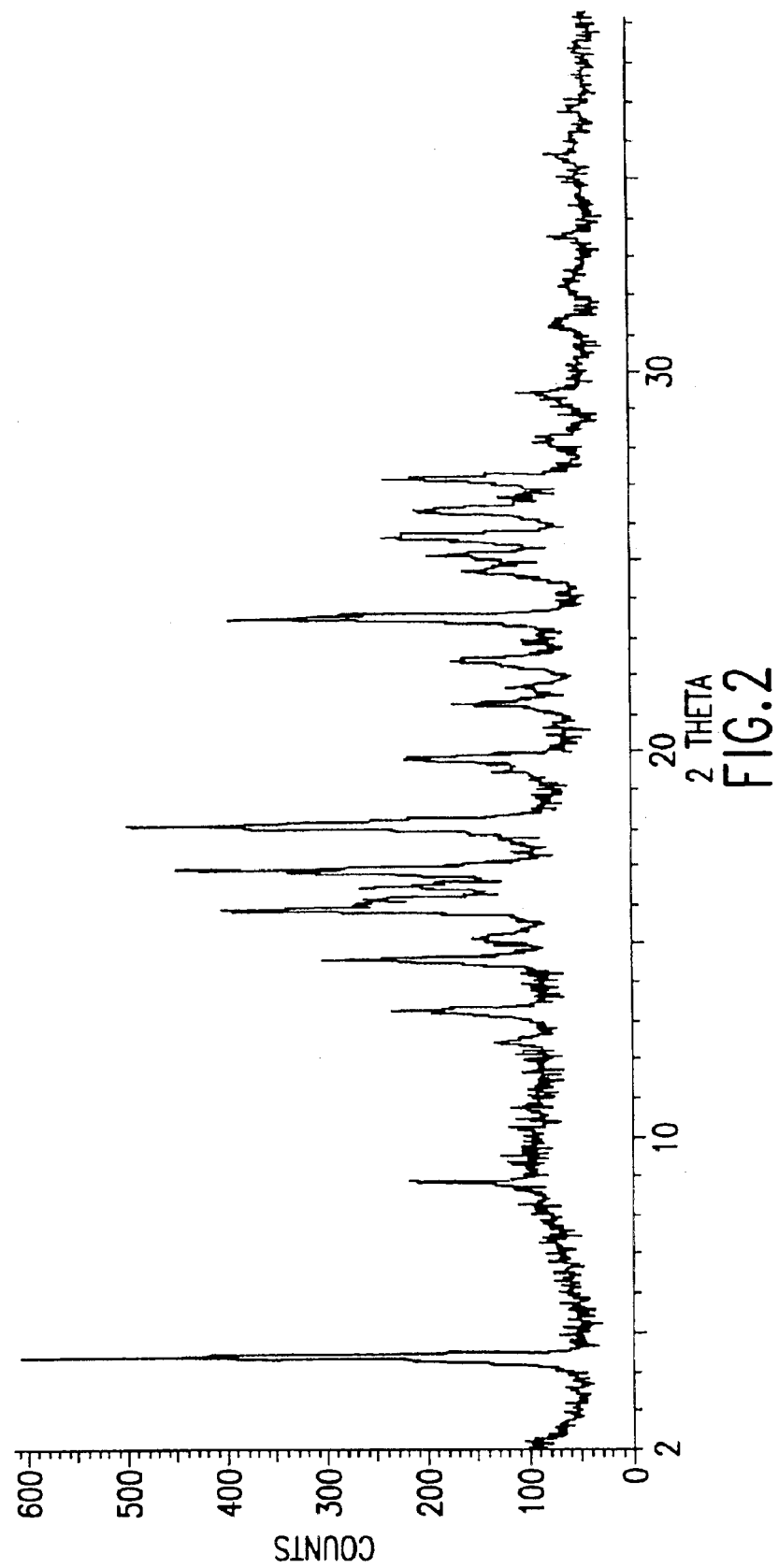
FIG. 2: X-ray powder diffraction pattern of the-free base (Form 2) of 4-[2-(5-cyano-thiazol-2-ylamino)-pyridin-4-ylmethyl]-piperazine-1-carboxylic acid methylamide.

The X-ray powder diffraction pattern of Forms 1 and 2 of the free base of 4-4 are indicative of a crystalline material with multiple diffraction peaks between 2° and 30° 2-theta. (FIGS. 1 and 2).

Thermal Properties

DSC

Differential Scanning Calorimetry (DSC) of Form 1 of the free base of Compound 4-4 from 20° C. to 350° C. at a heating rate of 10° C./min shows multiple thermal events.

TGA

Thermogravimetric Analysis (TGA) of Form 1 of the free base from 20° C. to 400° C. at a heating rate of 10° C./minutes shows a weight loss of 4.28% (theoretical loss of 4.8% for a monohydrate) between 50° C. and 150° C. The data suggest that the drug decomposes upon melting as determined by a sharp weight loss in the TGA at the melting temperature.

The X-ray powder diffraction patterns for the free bases (Forms 1 and 2) are illustrated in FIGS. 1 and 2. The X-ray powder diffraction data for these polymorphs are summarized below in the tables below:

| d-spacing (Å) | 2-theta (°) | relatively intensity (%) |
|---|---|---|
| Free Base (Form 1) | | |
| 19.95 | 4.42 | 52.4 |
| 9.89 | 8.93 | 36.2 |
| 6.96 | 12.69 | 31.4 |
| 6.60 | 13.39 | 40.3 |
| 6.33 | 13.95 | 68.4 |
| 6.12 | 14.44 | 41.9 |
| 5.73 | 15.44 | 66.3 |
| 5.63 | 15.72 | 100.0 |
| 5.33 | 16.60 | 44.9 |
| 4.83 | 18.31 | 45.1 |
| 4.47 | 19.84 | 42.2 |
| 4.12 | 21.55 | 44.9 |
| 3.88 | 22.86 | 24.8 |
| 3.77 | 23.54 | 62.0 |

-continued

| d-spacing (Å) | 2-theta (°) | relatively intensity (%) |
|---|---|---|
| 3.57 | 24.87 | 43.1 |
| 3.43 | 25.92 | 81.5 |
| 3.21 | 27.73 | 67.2 |
| 3.12 | 28.53 | 24.2 |
| Free Base (Form 2) | | |
| 20.54 | 4.29 | 100.0 |
| 10.12 | 8.72 | 36.2 |
| 7.15 | 12.35 | 22.3 |
| 6.71 | 13.16 | 39.2 |
| 6.10 | 14.50 | 50.6 |
| 5.88 | 15.05 | 25.8 |
| 5.59 | 15.83 | 66.9 |
| 5.51 | 16.06 | 40.6 |
| 5.38 | 16.44 | 44.0 |
| 5.25 | 16.84 | 71.9 |
| 4.91 | 18.04 | 81.7 |
| 4.49 | 19.73 | 36.7 |
| 4.19 | 21.15 | 28.2 |
| 3.98 | 22.27 | 29.2 |
| 3.79 | 23.41 | 65.3 |
| 3.60 | 24.65 | 26.4 |
| 3.55 | 25.05 | 32.5 |
| 3.48 | 25.57 | 40.6 |
| 3.39 | 26.25 | 35.1 |
| 3.28 | 27.11 | 40.5 |

What is claimed is:

1. Polymorph Form 1 of the free base of 4-[2-(5-cyano-thiazol-2-ylamino)-pyridin-4-ylmethyl]-piperazine-1-carboxylic acid methylamide characterized by an X-ray powder diffraction pattern having diffraction angles of: 4.42, 8.93, 12.69, 13.39, 13.95, 14.44, 15.44, 15.72, 16.60, 18.31, 19.84, 21.55, 22.86, 23.54, 24.87, 25.92, 27.73, and 28.53.

2. Polymorph Form 2 of the free base of 4-[2-(5-cyano-thiazol-2-ylamino)-pyridin-4-ylmethyl]-piperazine-1-carboxylic acid methylamide characterized by an X-ray powder diffraction pattern having diffraction angles of: 4.29, 8.72, 12.35, 13.16, 14.50, 15.05, 15.83, 16.06, 16.44, 16.84, 18.04, 19.73, 21.15, 22.27, 23.41, 24.65, 25.05, 25.57, 26.25, and 27.11.

3. A pharmaceutical composition that is comprised of the polymorph form in accordance with claim 1 and a pharmaceutically acceptable carrier.

4. A pharmaceutical composition that is comprised of the polymorph form in accordance with claim 2 and a pharmaceutically acceptable carrier.

5. The composition of claim 3 further comprising a second compound selected from:

1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

6. The composition of claim 5, wherein the second compound is another angiogenesis inhibitor selected from the group consisting of a tyrosine kinase inhibitor, an inhibitor of epidermal-derived growth factor, an inhibitor of fibroblast-derived growth factor, an inhibitor of platelet derived growth factor, an MMP inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, and an antibody to VEGF.

7. The composition of claim 5, wherein the second compound is an estrogen receptor modulator selected from tamoxifen and raloxifene.

* * * * *